United States Patent
Turner et al.

(10) Patent No.: US 8,136,728 B2
(45) Date of Patent: Mar. 20, 2012

(54) MEDICAL DEVICE TRACKING SYSTEM WITH TAG AND METHOD

(75) Inventors: Robin L. Turner, Memphis, TN (US); Thor M. Hanna, Memphis, TN (US); Sanjay Bisht, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 507 days.

(21) Appl. No.: 12/109,517

(22) Filed: Apr. 25, 2008

(65) Prior Publication Data

US 2009/0266889 A1    Oct. 29, 2009

(51) Int. Cl.
*G06F 17/60* (2006.01)
(52) U.S. Cl. ............ 235/385; 705/28; 206/363
(58) Field of Classification Search .......... 235/385; 705/28; 206/363
See application file for complete search history.

(56) References Cited

U.S. PATENT DOCUMENTS

| | | | |
|---|---|---|---|
| 4,154,342 A | 5/1979 | Wallace | |
| 4,501,363 A | 2/1985 | Isbey, Jr. | |
| 4,553,669 A | 11/1985 | Butterworth et al. | |
| 4,856,648 A | 8/1989 | Krueger | |
| 5,199,567 A | 4/1993 | Discko, Jr. | |
| 5,636,736 A | 6/1997 | Jacobs et al. | |
| 5,759,028 A | 6/1998 | Bozman | |
| 5,762,192 A | 6/1998 | Jacobs et al. | |
| 5,887,707 A | 3/1999 | Anascavage et al. | |
| 5,934,460 A | 8/1999 | Schmid | |
| 5,967,305 A | 10/1999 | Blonder et al. | |
| 6,328,746 B1 | 12/2001 | Gambale | |
| 6,373,786 B1 | 4/2002 | Kagan et al. | |
| 6,375,956 B1 | 4/2002 | Hermelin et al. | |
| 6,415,916 B1 | 7/2002 | Rini | |
| 7,048,120 B2 | 5/2006 | Pond | |
| 7,118,029 B2 | 10/2006 | Nycz et al. | |
| 7,213,767 B2 | 5/2007 | Tethrake et al. | |
| 7,256,699 B2 | 8/2007 | Tethrake et al. | |
| 7,268,684 B2 | 9/2007 | Tethrake et al. | |
| 7,338,282 B2 | 3/2008 | Corcoran | |
| 7,362,228 B2 | 4/2008 | Nycz et al. | |
| 2002/0004660 A1 | 1/2002 | Henniges | |
| 2004/0243207 A1 | 12/2004 | Olson | |
| 2005/0033430 A1 | 2/2005 | Powers et al. | |
| 2006/0144749 A1 | 7/2006 | Arnold | |
| 2006/0145871 A1 | 7/2006 | Donati | |
| 2006/0244652 A1 | 11/2006 | Tethrake et al. | |
| 2006/0260958 A1 | 11/2006 | Brunner | |
| 2007/0001839 A1 | 1/2007 | Cambre et al. | |

(Continued)

FOREIGN PATENT DOCUMENTS

DE    202007004638    6/2007

(Continued)

OTHER PUBLICATIONS

Orthopedics This Week, vol. 4, Issue 4, p. 4, Feb. 5, 2008, "Radio Frequency Identification and Orthopedics."

(Continued)

*Primary Examiner* — Allyson N Trail

(57) ABSTRACT

Embodiments of the invention include systems and methods for tracking a medical device. Systems configured for such tracking may include the capability to either or both detect tampering with the medical device and to effectively expose the medical device to sterilization substances while the medical device is captured by a mechanism including an identifying characteristic.

10 Claims, 9 Drawing Sheets

U.S. PATENT DOCUMENTS

| | | |
|---|---|---|
| 2007/0095689 A1 | 5/2007 | Pratt et al. |
| 2007/0125392 A1 | 6/2007 | Olson et al. |
| 2007/0144926 A1 | 6/2007 | Bettenhausen et al. |
| 2007/0159337 A1 | 7/2007 | Tethrake et al. |
| 2007/0188306 A1 | 8/2007 | Tethrake et al. |
| 2007/0205126 A1 | 9/2007 | Elsener |
| 2007/0239289 A1 | 10/2007 | Cambre et al. |
| 2007/0284428 A1 | 12/2007 | Cambre et al. |
| 2008/0048855 A1 | 2/2008 | Berger |
| 2008/0230421 A1 | 9/2008 | Pleil et al. |
| 2008/0230422 A1 | 9/2008 | Pleil et al. |
| 2008/0230423 A1* | 9/2008 | Loeffler et al. .............. 206/438 |
| 2009/0118831 A1 | 5/2009 | Trieu |
| 2009/0266890 A1* | 10/2009 | Bagozzi et al. .............. 235/385 |

FOREIGN PATENT DOCUMENTS

| | | |
|---|---|---|
| EP | 1842505 | 10/2007 |
| JP | 2008052013 | 3/2008 |
| KR | 10-2006-0102826 | 9/2006 |
| WO | 2006124188 | 11/2006 |

OTHER PUBLICATIONS

International Searching Authority, ISR and Written Opinion, Jul. 31, 2009.

International Search Report in related Application No. PCT/US2009/041760 mailed Aug. 11, 2009.

* cited by examiner

MEDICAL DEVICE TRACKING SYSTEM WITH TAG AND METHOD

FIELD OF THE INVENTION

The present invention relates generally to the field of identification and tracking of parts, and more particularly relates to associating a medical device with an identification tag and tracking the medical device.

BACKGROUND

Implantable medical devices must be sterile prior to use in order to reduce the risk of infection in patients receiving such devices. Generally, there are two ways to provide sterile surgical devices. One way is to sterilize a device to be implanted immediately prior to implantation. Another way is to sterilize a device during the manufacturing process, and then to ship the device to a user in a sterilized condition. The first way is typically called providing a device "non-sterile," because the manufacturer ships the device in a condition that is not adequately sterilized for implantation. The second way is typically called providing a device "sterile," because the device is ready for implantation when shipped from the manufacturer.

There is a strong and growing need to track medical devices from their base materials and manufacture to their use, and throughout the intervening time. Tracking of medical devices may also be referred to as maintaining traceability of the devices. It is sometimes important to track medical devices so that patients can be notified of any information related to the safety or longevity of devices once implanted. The U.S. Food and Drug Administration is currently considering requiring that implantable medical devices be uniquely identified and tracked through the time of use of the devices.

It is relatively straightforward to uniquely identify and track sterile medical devices. Unique labels or other indicia are applied to the product and the labels or other indicia remain associated with the medical device until the device is used. In some instances, sterile product labels include adhesive portions that can be applied to a chart or file of a patient to conveniently associate the sterile medical device with a particular patient.

Non-sterile products provide a greater tracking challenge, although there are several reasons for preferring non-sterile shipment of medical devices. A larger number of non-sterile devices can be provided in groups or sets that present the devices in a manner where the devices are readily available for use. The large number of devices may represent a large number of sizes and optional configurations that provide surgeons with many alternatives in a convenient arrangement. Devices that are not used are simply returned to stock for sterilization prior to a subsequent use. Non-sterile devices do not have a definitively limited shelf life, as sterile products do. Non-sterile devices are less expensive to package and sterilize. Non-sterile devices can typically be more densely packaged into a common carrier than sterile devices. The primary reason that such non-sterile products are difficult to track, however, is that the products are difficult to mark, may not be marked at all, and may be identical to other products with which they are packaged, thus creating a possibility of confusion among parts. In many instances, specific non-sterile products are not tracked beyond their manufacturing facility, and may only be counted when reconciled for payment as one of many products that were not returned to a manufacturer for replenishment.

One way of tracking non-sterile medical devices would be to associate the devices with a component or mechanism that includes identifying information. Such a component or mechanism may advantageously provide ready access to the device by sterilizing material such as steam or other cleaning solutions. It would also be advantageous in some tracking systems for non-sterile implants to be resistant to intentional or even incidental tampering that could disassociate identifying information from a medical device.

SUMMARY

An embodiment of the invention is a medical device tracking system. The system includes a medical device, a first component, and a second component coupled with the first component to capture the medical device. A tracking device may be associated with the first component or the second component. A portion of the medical device completely extends from the first component to expose the medical device when the medical device is captured by the first and second components.

Another embodiment of the invention is a medical device tracking system that includes a medical device and a capture mechanism removably coupled to the medical device. The capture mechanism includes a body capable of multiple sterilizations without degradation, and an identification tag associated with the body. The capture mechanism is configured such that removal of the medical device from the capture mechanism is thereafter detectable.

Yet another embodiment of the invention is a method of tracking a medical device. The method includes capturing the medical device in a mechanism that has an identifier. The mechanism is configured such that removal of the medical device from the mechanism is thereafter detectable. The method also includes transferring the mechanism and captured medical device to a potential user and specifying sterilization of the medical device prior to potential implantation of the medical device. Further, the method includes accepting return of the mechanism and captured medical device and transferring the mechanism and captured medical device to the potential user or another user.

Still another embodiment of the invention is a method of tracking a medical device. To accomplish the method embodiment, a medical device and instructions specifying steam sterilization of the medical device prior to implantation of the medical device into a patient are provided. The method further includes inserting a portion of the medical device into a first segment of an identification tag and out of a second segment of the identification tag such that the medical device is at least partially exposed beyond a perimeter of the identification tag to receive steam sterilization. The medical device may also be locked into the identification tag such that separation of the medical device from the identification tag is reliably detectable.

DETAILED DESCRIPTION

Figure 1:
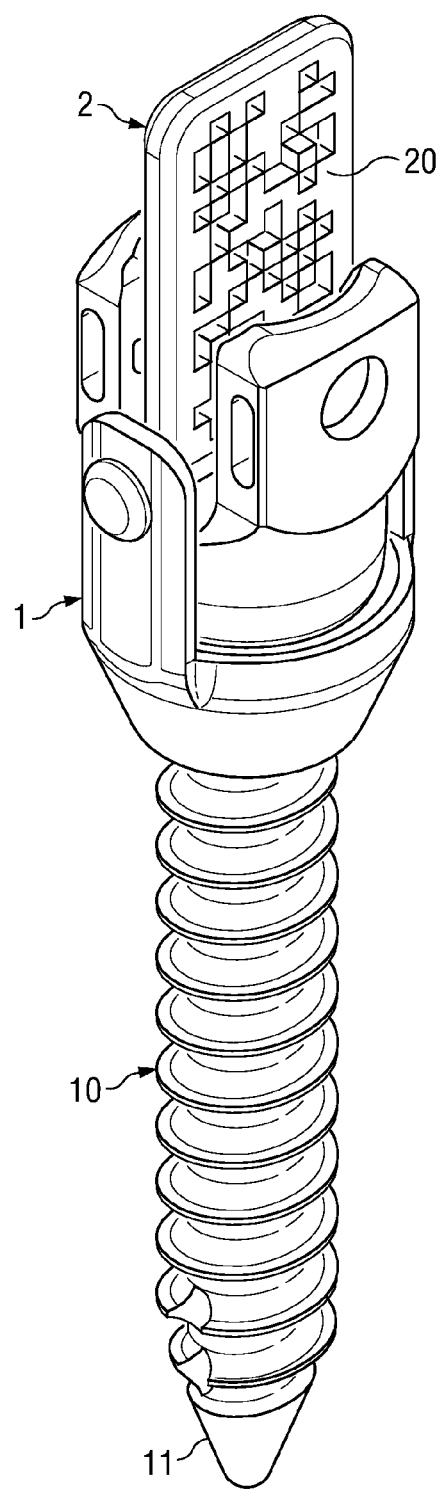
FIG. 1 is a perspective view of an embodiment of the invention that illustrates a tracking system including a spinal pedicle screw.
Figure 2:
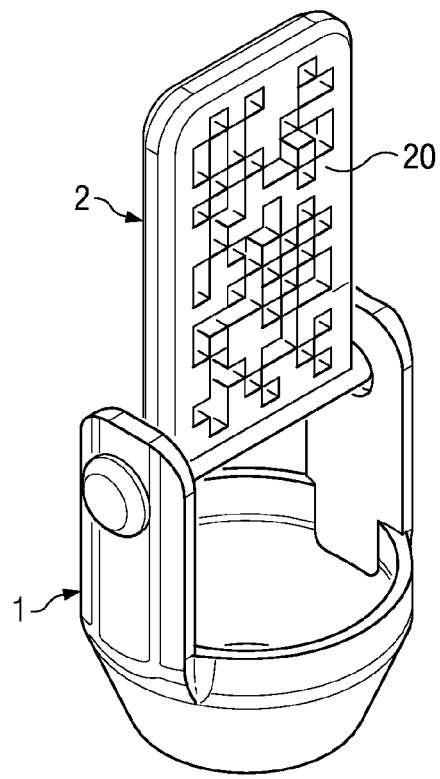
FIG. 2 is s perspective view of capture components of FIG. 1 with the spinal pedicle screw removed for clarity.

FIG. 1 illustrates a medical device tracking system embodied in a spinal surgical screw 10 medical device that is captured by a first component 1 and a second component 2. As illustrated, a tracking device 20 is associated with the second component 2 as a two dimensional bar code marking on a side of the second component 2.

The medical device of this or any other embodiment of the invention may be any implant or instrument used in accomplish a medical procedure. The medical device of some embodiments is capable of undergoing one or more steam sterilization cycles, or other sterilization procedures, without degrading in a manner that would make the implant unsuitable for use in a medical procedure. The medical device of this or any other embodiment of the invention may consist of materials, by way of example, and without limitation, including titanium and its alloys, ASTM material, cobalt chrome, tantalum, ceramic, poly-ether-ether-ketone (PEEK), PEAK, various plastics, plastic composites, carbon fiber composites, coral, allograft, autograft, zenograft, and can include artificial materials which are at least in part bioresorbable, or any material suitable for human implantation.

Figure 7:
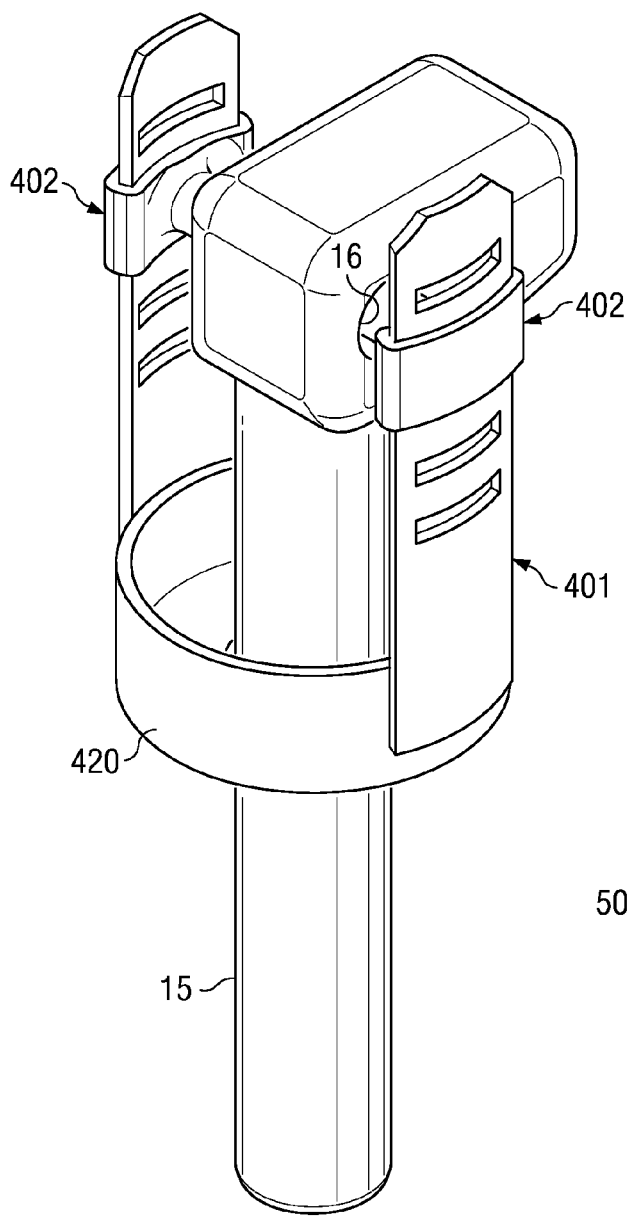
FIG. 7 is a perspective view of an embodiment of the invention that illustrates a tracking system including a spinal sagittal rod.
Figure 11:
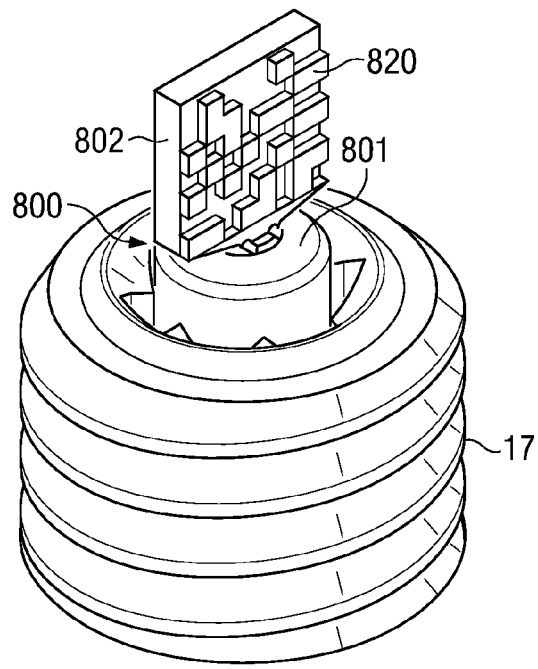
FIG. 11 is a perspective view of an embodiment of the invention that illustrates a tracking system including a spinal set screw.

In addition to being a surgical screw, the medical device may be a spinal sagittal rod 15, as illustrated in FIG. 7, or a set screw 17, as illustrated in FIG. 11. The medical device of some embodiments may be, without limitation, a surgical screw of any variety, a spinal or other orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, or other spinal fixation instrumentation, an intramedullary nail, an external fixation device, a hip prosthesis or therapeutic device, a knee prosthesis or therapeutic device, or an instrument useful with any of the previously recited devices.

The tracking device 20, or any tracking device herein, may be any device that is capable of retaining identifying information. In some embodiments, the tracking device is a device suitable for scanning by an optical scanner such as a one or two dimensional bar code reader. The tracking device may also be a radio frequency identification (RFID) device that is readable through radio frequency transmission generated by an independently powered RFID device. The tracking device may be an RFID device that includes a transponder and is readable in response to a radio frequency signal transmitted to the RFID device. In some embodiments, the tracking device is a human readable visual and/or tactile device such as, but not limited to, alphanumeric characters, and may optionally include raised or lowered portions. The tracking device may also be a printed or written item in combination with a slot or groove in a component of the system, whereby the printed or written item is placed in the slot or groove to display information. A tracking device may also be applied as an adhesive label. Some embodiments of an adhesive label are resistant to sterilization procedures, including steam sterilization.

In some embodiments, a portion of the medical device completely extends from the first component to expose the medical device. Exposure, as used herein, may include extending all or a part of one or more segments of the medical device from capturing components. As illustrated in FIG. 1, a distal end 11 of the surgical screw 10 extends from the first component 1 when the medical device is captured by the first and second components 1, 2. A portion of the surgical screw 10 proximal to the distal end 11 is captured between coupled first and second components 1, 2. The first and second components 1, 2 may be removed from one another by twisting, pulling, or otherwise creating stress between the components, or between one or both of the components and the captured medical device. Alternatively, the first and second components 1, 2 may be removed by cutting or otherwise degrading a portion of one or both of the first and second components 1, 2 or a connection between the components.

Figure 3:
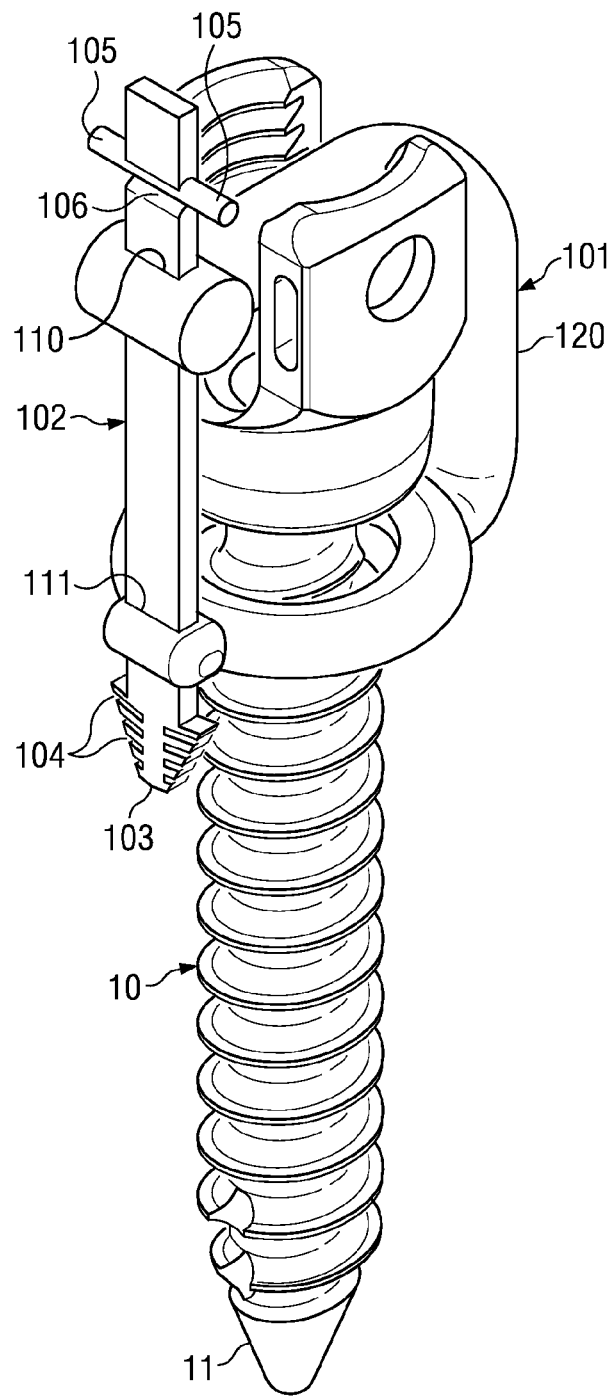
FIG. 3 is a perspective view of an embodiment of the invention that illustrates a tracking system including a spinal pedicle screw.

As shown in FIG. 3, a spinal surgical screw 10 is captured by a first component 101 and a second component 102. The illustrated embodiment also includes a tracking device 120 in the second component 102. In other embodiments, a tracking device may be incorporated in the first component 101, or another part of a mechanism. A distal end 11 of the surgical screw 10 extends from the first component 101 when the medical device is captured by the first and second components 101, 102. A portion of the surgical screw 10 proximal to the distal end 11 is captured between coupled first and second components 101, 102. The second component 102 shown in FIG. 3 includes an insertion end 103 that includes relief cuts 104 that permit portions of the insertion end 103 to deflect as they are inserted through first and second connection slots 110, 111 in the first component 101. Once inserted, removal of the second component 102 from the first and second connection slots 110, 111 in the opposite direction from insertion may cause fractures to develop within the insertion end 103. The second component 102 also includes a pair of stops 105 that prevent insertion of the second component 102 completely through the first connection slot 110. Forced removal of the second component 102 by continued progress in the direction of insertion would be detectable because such an action would shear the stops 105 from the second component 102. The second component 102 is also provided with a notch 106 that enables a user to grasp the second component 102 and twist, bend, pull, or otherwise create stress and fracture the second component 102 at the notch 106. Subsequently, removal of the second component 102 from the first component 101 would be easily accomplished, and the spinal surgical screw 10 could be removed. The fractured second component 102 would be detectable indicia of decoupling of the first and second components 101, 102.

Figure 4:
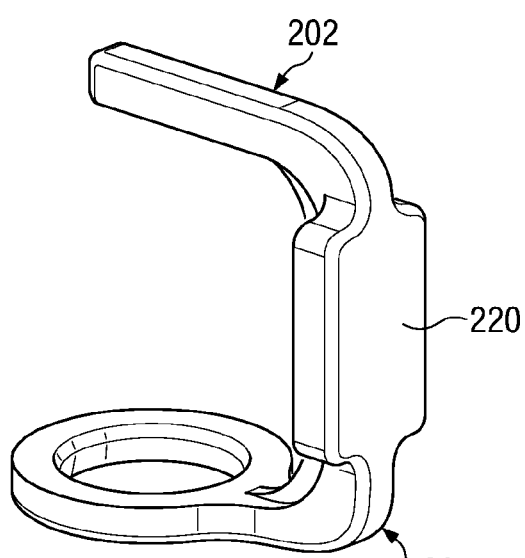
FIG. 4 is a perspective view of a component of a tracking system.

FIG. 4 illustrates first and second components 201, 202 that are integrated into a unit mechanism. A tracking device 220 is also integrated into the mechanism. The illustrated mechanism is configured to leave detectable indicia when a medical device is removed from the mechanism. The mechanism may be applied to a spinal surgical screw, for example, in a manner essentially similar to the system shown in FIG. 3. In some embodiments, the mechanism, once placed around a medical device, is chemically or thermally treated to be less tolerant of mechanical strain such that removing the mechanism from the medical device will result in a fracture of a portion of one or both of first and second components 201, 202. Alternatively, removal of the mechanism from the medical device may result in discoloration or permanent distortion of the first or second components 201, 202. In another embodiment, the medical device may be assembled within the first and second components 201, 202 such that separation of the assembled medical device from the first and second components 201, 202 will leave detectable indicia. Similarly, any of first and second components 1, 2; 101, 102; 301, 302; 401, 402; 501, 502; 701, 702; 801, 802; 901, 902; and 1001, 1002 may be integrated into a unit mechanism in some embodiments.

Figure 5:
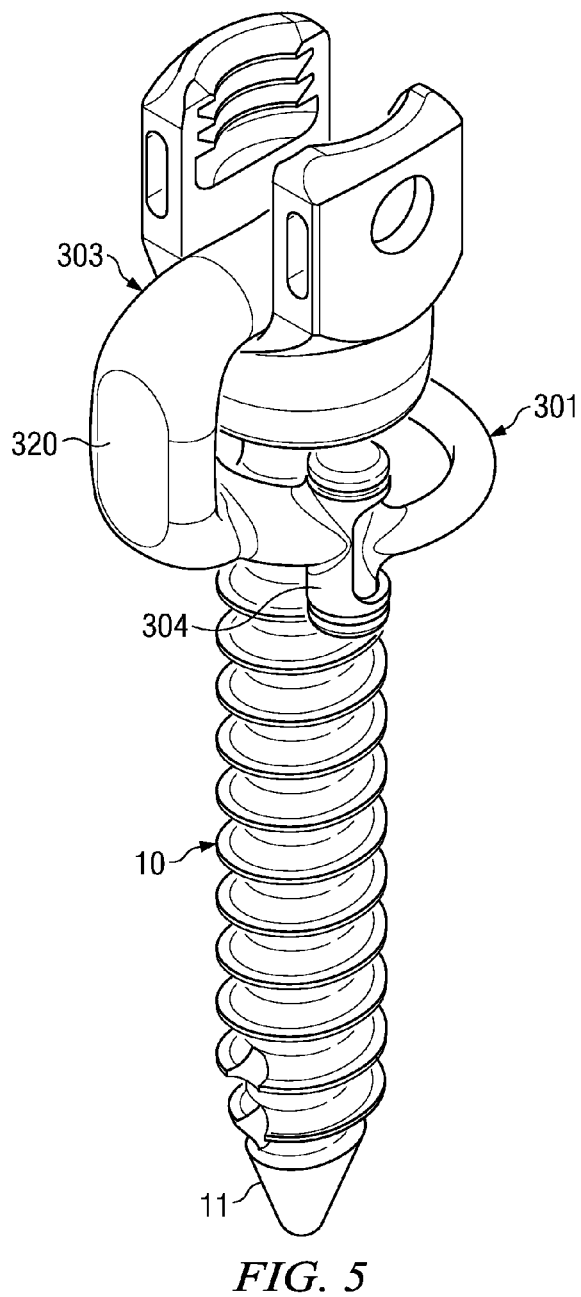
FIG. 5 is a perspective view of an embodiment of the invention that illustrates a tracking system including a spinal pedicle screw.
Figure 6:
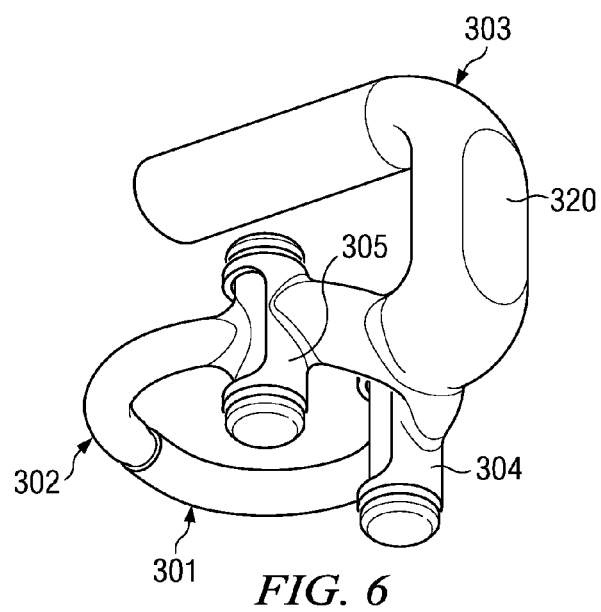
FIG. 6 is s perspective view of capture components of FIG. 5 with the spinal pedicle screw removed for clarity.

FIGS. 5 and 6 in combination show a mechanism for capturing a spinal surgical screw 10 that includes of a first component 301 and a second component 302 that are coupled together at one of their respective ends, and that connect to a third component 303 at their respective opposite ends. The connection between the illustrated first component 301 and the third component 303 is through a first hinge 304, and the connection between the illustrated second component 302 and the third component 303 is through a second hinge 305. A tracking device 320 is shown integrated into the third component 303. As illustrated in FIG. 5, a distal end 11 of the spinal surgical screw 10 extends from the first component 301 when the medical device is captured by the first and second components 301, 302 in combination with the third component 303. A portion of the surgical screw 10 proximal to the distal end 11 is captured between coupled first and second components 301, 302.

In the embodiment illustrated in FIGS. 5 and 6, the coupling between the first component 301 and the second component 302 is accomplished after a medical device such as the spinal surgical screw 10 is placed within the grasp of the first and second components 301, 302. The spinal surgical screw 10 may be inserted when the first and second components 301, 302 are hinged open about their respective hinges 304, 305. Once the spinal surgical screw 10 is positioned within the grasp of the first and second components 301, 302, the components are rotated about respective first and second hinges 304, 305 to couple a first end of each component with the other component. This coupling may be such that decoupling the first and second components 301, 302 relative to one another may not be accomplished without creating a detectable indication of the decoupling. The decoupling may result in fracture of one or more of the first component 301, the second component 302, the third component 303, the first hinge 304, the second hinge 305, and any of the joints between these parts, or any part, of the mechanism.

In FIG. 7, a medical device tracking system embodied in a spinal sagittal rod 15 that is captured by a first component 401 and a second component 402 is shown. A tracking device 420 may be associated with the first component 401, as is illustrated, or with other components. The second component 402 engages a through-hole 16 in the spinal sagittal rod 15 and is coupled to the first component 401 to capture the spinal sagittal rod 15. Similar arrangements are contemplated by embodiments of the invention for other devices having a through-hole through which a component may be passed to capture the devices.

Figure 8:
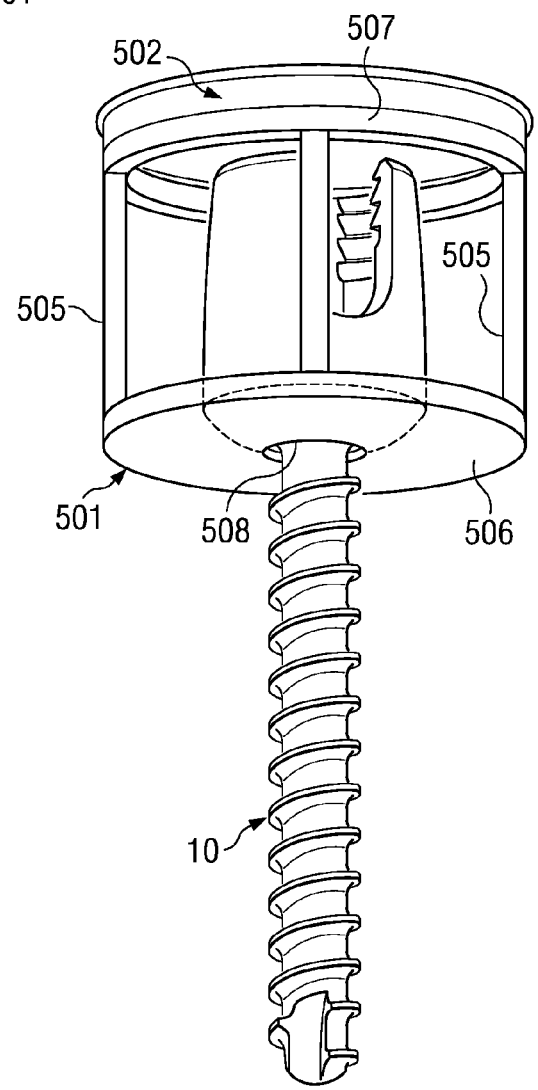
FIG. 8 is a perspective view of an embodiment of the invention that illustrates a tracking system including a spinal pedicle screw.

FIG. 8 depicts a medical device tracking system embodied in a spinal surgical screw 10 that is captured by a first component 501 and a second component 502. A tracking device 520 of any of the types previously disclosed herein may be associated with the second component 502 or the first component 501. In some embodiments, the second component 502 is coupled to the first component 501 by a snap fit around all or a portion of the contact surface between the components. The second component 502 and the first component 501 may also be coupled in part by a hinge between the components, or with threads between the components. The first and second components 501, 502 are depicted as generally round through a horizontal cross-section, but they may be rectangular or any other operable shape. The first component 501 shown includes vertical struts 505 that connect between a base 506 and an upper rim 507. The struts 505 may be rigid or flexible and may be continuous around the perimeter of the first component, or spaced intermittently as shown in FIG. 8. The illustrated base 506 has a bore 508 for receiving the spinal surgical screw 10. The bore 508 may be a part of the base 506, as shown, or may be an opening at the terminus of two or more vertical struts 505.

Figure 9:
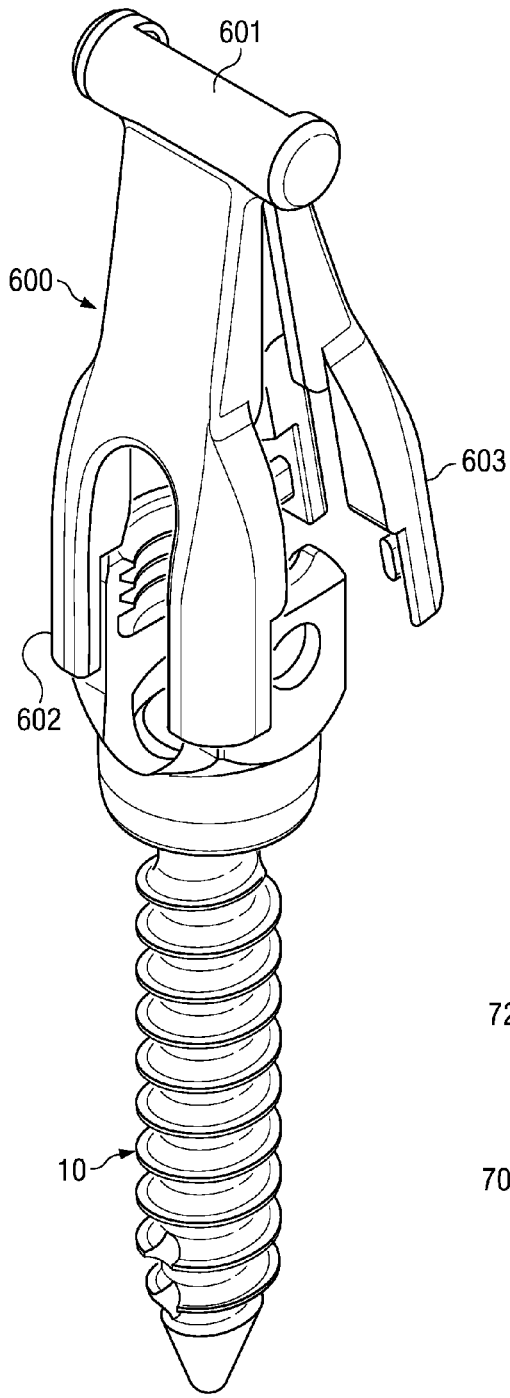
FIG. 9 is a perspective view of an embodiment of the invention that illustrates a tracking system including a spinal pedicle screw.

A medical device tracking system is illustrated in FIG. 9 that includes a medical device in the form of a spinal surgical screw 10 and a capture mechanism 600 removably coupled to the medical device. The capture mechanism 600 is a body capable of multiple fluid sterilizations without degradation. For example, the capture mechanisms 600 of various embodiments would not undergo meaningful loss of structural integrity, would not be discolored, or would not lose information retained on the mechanisms 600 as a result of multiple fluid sterilizations. The sterilizations may be from steam sterilization or from application of a chemical sterilizing substance, or from any other effective sterilization substance or process. An identification tag, indicia, or other marking is associated with the body. The capture mechanism 600 is configured such that removal of the medical device from the capture mechanism 600 is thereafter detectable. This may be accomplished, for example, by configuring a ratcheting hinge 601 between branches 602, 603 that must be fractured to separate branches 602, 603 once the branches have been brought together to capture the spinal surgical screw 10 between them. In other embodiments, an additional member may be wrapped around or connected between branches 602 and 603 as a mechanism for detecting whether the branches have been separated after being closed around the spinal surgical screw 10 or other medical device. The additional member or the hinge 601 of some embodiments are configured to at least one of rupture, non-resiliently deform, or change color when the capture mechanism 600 is removed from a medical device that has been captured within the capture mechanism 600. A rupture can be a full or partial rupture of all or a part of the capture mechanism 600. Likewise, a non-resilient deformation may be a change in the shape of any part of the capture mechanism 600 that remains thereafter in whole or in part detectable. A discoloration may occur, for example and without limitation, when a polymer material undergoes plastic material deformation. A tracking device of any of the types previously disclosed may be associated with the capture mechanism 600.

Figure 10:
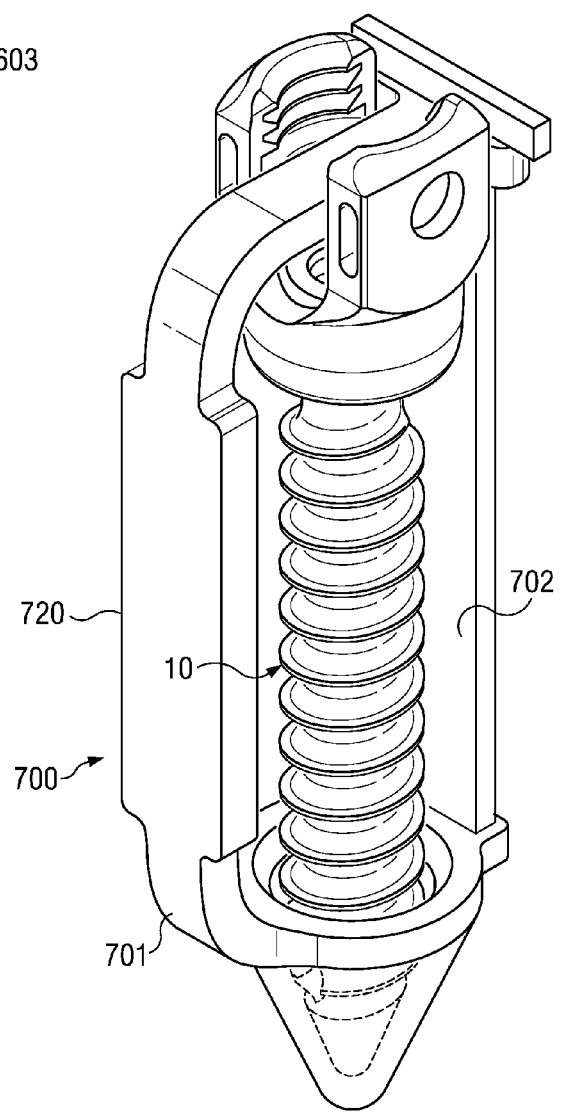
FIG. 10 is a perspective view of an embodiment of the invention that illustrates a tracking system including a spinal pedicle screw.

FIG. 10 shows a medical device tracking system that includes a medical device in the form of a spinal surgical screw 10 and a capture mechanism 700 removably coupled to the medical device. The capture mechanism 700 is a body capable of multiple sterilizations without degradation. An identification tag 720, indicia, or other marking is associated with the body. The capture mechanism 700 is configured such that removal of the medical device from the capture mechanism 700 is thereafter detectable. In some embodiments, the capture mechanism 700 has a first component 701 that captures both ends of the spinal surgical screw 10 or other medical device. To place the spinal surgical screw 10 within the first component 701, the first component must be flexed and placed over the respective ends of the spinal surgical screw. To effectively capture the spinal surgical screw 10, a second component 702 is coupled with the first component 701. The capture mechanism 700 shown is then configured such that removal of the spinal surgical screw 10 from the capture mechanism 700 is thereafter detectable. As illustrated, this is accomplished in combination with the second component 702 that, once inserted, is not removable from the first component 701 without detectable alteration occurring to one or both of the first and second components 701, 702. For example, one or both of the first and second components 701, 702 are configured to at least one of rupture, non-resiliently deform, or change color when the capture mechanism 700 is separated from the spinal surgical screw 10.

FIG. 11 shows a medical device tracking system that includes a medical device in the form of a spinal set screw 17 and a capture mechanism 800 removably coupled to the medical device. The capture mechanism 800 is a body capable of multiple sterilizations without degradation. An identification tag 820 or other marking is associated with the body. The capture mechanism 800 is configured such that removal of the spinal set screw 17 from the capture mechanism 800 is thereafter detectable. In the illustrated embodiment, the capture mechanism 800 has a first component 801 that penetrates an opening in the spinal set screw 17. To effectively capture the spinal set screw 17, a second component 802 is coupled with the first component 801. The capture mechanism 800 shown is then configured such that removal of the medical device from the capture mechanism 800 is thereafter detectable. As illustrated, this is accomplished by the second component 802 that, once inserted, is not removable from the first component 801 without detectable alteration occurring to one or both of the first and second components 801, 802. For example, one or both of the first and second components 801, 802 are configured to at least one of rupture, non-resiliently deform, or change color when the capture mechanism 800 is separated from the spinal set screw 17.

Figure 12:
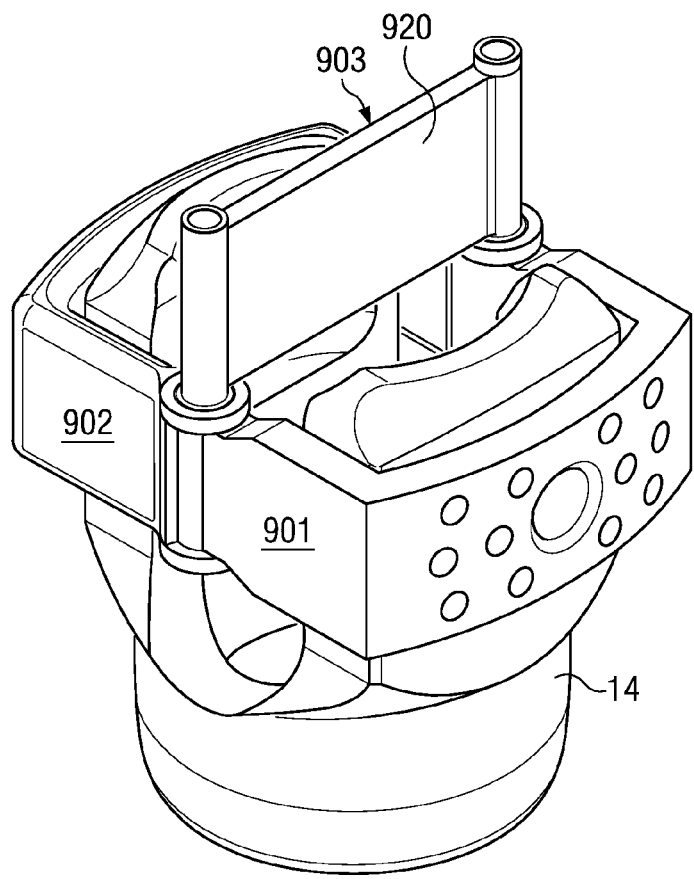
FIG. 12 is a perspective view of an embodiment of the invention that illustrates a tracking system including a spinal pedicle screw head.

FIG. 12 shows a mechanism for capturing a spinal surgical screw head 14 that includes of a first component 901 and a second component 902 that are coupled together at two of their respective ends. A third component 903 provides pins for the coupling between the first component 901 and the second component 902 in the illustrated embodiment. A tracking device 920 is shown integrated into the third component 903. As illustrated in FIG. 12, a portion of the spinal surgical screw head 14 is between and a portion extends from the first and second components 901, 902 when the medical device is captured by the first and second components 901, 902 in combination with the third component 903.

In the embodiment illustrated in FIG. 12, the coupling between the first component 901 and the second component 902 is accomplished after a medical device, such as the spinal surgical screw head 14, is placed between the first and second components 901, 902. The spinal surgical screw head 14 may be placed between separated first and second components 901, 902, and then the first and second components are moved together to align the holes at their respective ends. With all holes aligned, the third component 903 may be inserted into the holes at the ends of the first and second components 901, 902 to pin the components together as an assembly. This coupling may be such that decoupling the first and second components 901, 902 relative to one another may not be accomplished without creating a detectable indication of the decoupling. The decoupling may result in fracture of one or more of the first component 901, the second component 902, the third component 903, and any of the joints between these parts, or other parts, of the mechanism. The decoupling may also result in discoloration, distortion, or any other detectable indication of decoupling or tampering with the spinal surgical screw head.

Figure 13:
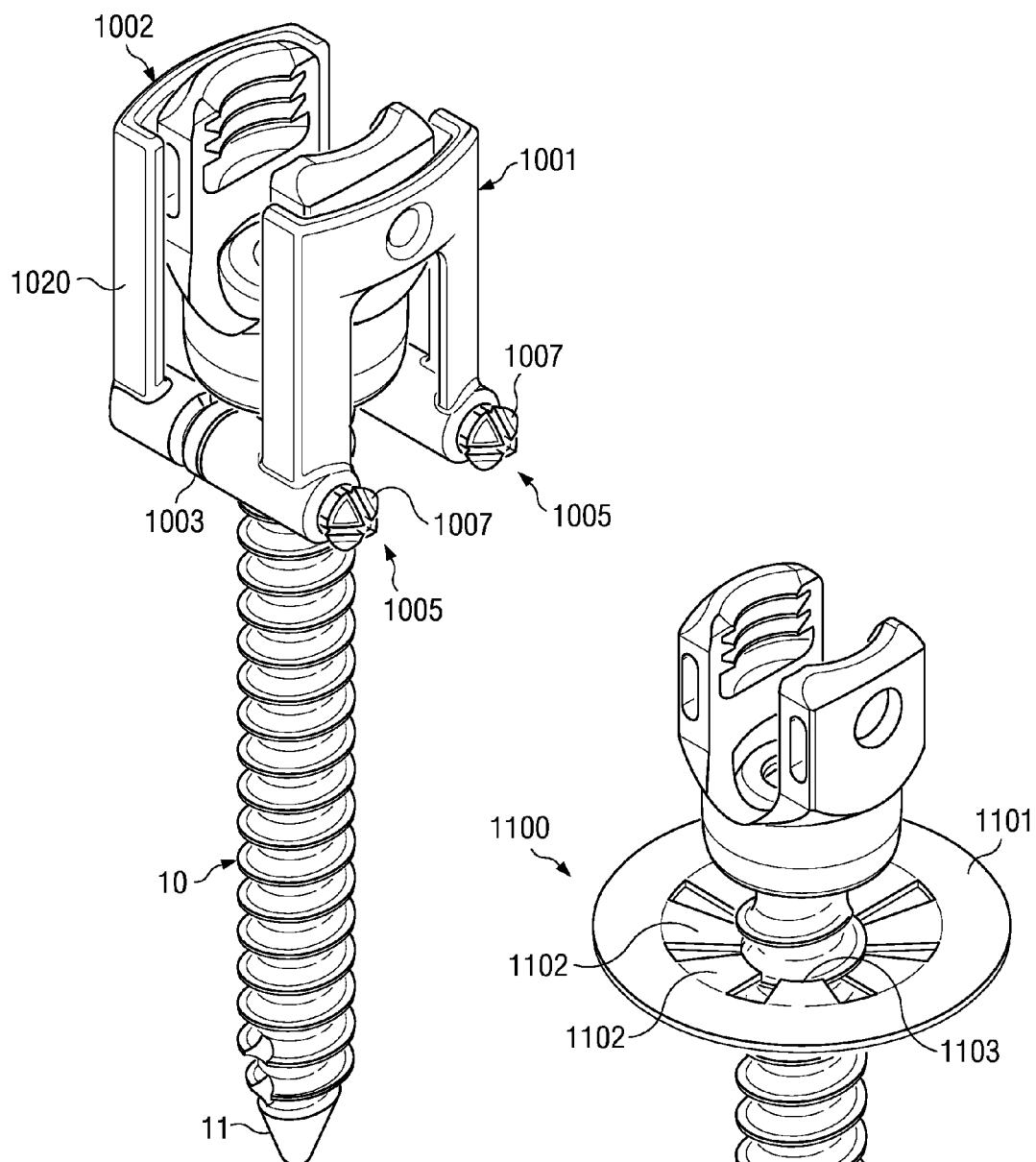
FIG. 13 is a perspective view of an embodiment of the invention that illustrates a tracking system including a spinal pedicle screw.

FIG. 13 shows a mechanism for capturing a spinal surgical screw 10 that includes of a first component 1001 and a second component 1002 that are coupled together at two of their respective ends. A third component 1003 provides a pin for the coupling between the first component 1001 and the second component 1002 in the illustrated embodiment. As shown, there are two third component 1003 pins for coupling the first component 1001 to the second component 1002. Each third component 1003 pin includes a distal end 1005. Each distal end 1005 includes at least one shoulder 1007. In operation, the third component 1003 may be locked with the first component 1001 by pushing the distal end 1005 through an opening in the first component 1001. Once through the opening, the shoulder 1007 prevents the distal portion 1005 of the third component 1003 from being easily removed from the first component 1001, and thereby securing the spinal surgical screw 10 between the first component 1001 and the second component 1002. In some embodiments, two pins may be integrated into a single component attached at their proximal ends. The third component 1003 may also be integrated with the second component 1002 in a unitary body in some embodiments.

A tracking device 1020 is shown integrated into the second component 1002, and may be a part of any other portion of the mechanism in other embodiments. As illustrated in FIG. 13, a portion of the spinal surgical screw 10 is between, and a portion extends from, the first and second components 1001, 1002 when the medical device is captured by the first and second components 1001, 1002 in combination with the third component 1003.

In the embodiment illustrated in FIG. 13, the coupling between the first component 1001 and the second component 1002 is accomplished after a medical device, such as the spinal surgical screw 10, is placed between the first and second components 1001, 1002. The spinal surgical screw 10 may be placed between separated first and second components 1001, 1002, and then the first and second components are moved together to align the holes at their respective ends. With all holes aligned, the third component 1003 may be inserted into the holes at the ends of the first and second components 1001, 1002 to pin the components together as an assembly. This coupling may be such that decoupling the first and second components 1001, 1002 relative to one another may not be accomplished without creating a detectable indication of the decoupling. The decoupling may result in fracture of one or more of the first component 1001, the second component 1002, the third component 1003, and any of the joints between these parts, or other parts, of the mechanism. The decoupling may result in discoloration, distortion, or any other detectable indication of decoupling or tampering with the spinal surgical screw head.

The coupling between the first and second components 1, 2; 101, 102; 201, 202; 301, 302; 401, 402; 501, 502; 701, 702; 801, 802; 901, 902; and 1001, 1002 of some embodiments is such that once the components are coupled together, then separation of the components is detectable. This may be accomplished, without limitation, by applying adhesive between the components, by providing ratcheting or snap-fit connections designed to fracture relatively easily as compared to other portions of the mechanism when stressed, by melting, welding, or otherwise joining all or a portion of the components together, and by including a indicator device across a joint between or through the components that fracture, change shape, change color, or otherwise are altered by separation of the first and second components. Detectable separation of the components may occur at one or more connections between the components, or may include fracture or change within either or both of the first and second components. In some embodiments, the first and second components, and in some instances other components, form a capture mechanism configured such that removal of the medical device from the capture mechanism is detectable as specifically described, or in another manner.

Figure 14:
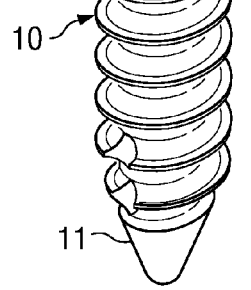
FIG. 14 is a perspective view of an embodiment of the invention that illustrates a tracking system including a spinal pedicle screw.

FIG. 14 illustrates a medical device tracking system that includes a medical device in the form of a spinal surgical screw 10 and a capture mechanism 1100 removably coupled to the medical device. The capture mechanism 1100 is a body capable of multiple fluid sterilizations without degradation. For example, the capture mechanisms 1100 of various embodiments would not undergo meaningful loss of structural integrity, would not be discolored, or would not lose information retained on the mechanisms 1100 as a result of multiple fluid sterilizations. The sterilizations may be from steam sterilization or from application of a chemical sterilizing substance, or from any other effective sterilization substance or process. An identification tag, indicia, or other marking is associated with the body. The capture mechanism 1100 is configured such that removal of the medical device from the capture mechanism 1100 is thereafter detectable.

The illustrated capture mechanism 1100 includes a periphery 1101 and fingers 1102. The periphery 1101 may be continuous around a perimeter, as shown, or may only be a partial enclosure. The periphery 1101 shown is generally round, but in other embodiments may be any shape that would function to support one or more fingers. Alternatively, multiple capture mechanism may be linked or formed together to create an array for accepting medical devices. The number of fingers 1102 may vary with other embodiments. In the embodiment shown, one or more of the fingers 1102 is attached to the periphery 1101 to permit insertion of the spinal surgical screw 10 through the capture mechanism 1100 by first inserting the distal end 11 through the capture mechanism 1100. The free end 1103 of each finger 1102 is biased toward the distal end 11 of the spinal surgical screw 10 as shown. This configuration permits each finger 1102 to be relatively easily bent to allow passage of the spinal surgical screw 10. However, if the spinal surgical screw 10 is withdrawn from the capture mechanism 1100, the free ends 1103 of one or more of the fingers 1102 are pointed, at least in part, in opposition to the removal of the spinal surgical screw 10 and create a force in one or more of the fingers 1102. The force created is more significant than the force in a finger 1102 associated with insertion of the spinal surgical screw 10 into the capture mechanism 1100 because of the orientation of the fingers 1102. Therefore, reaction to forces applied may be incorporated in one or more of the fingers 1102 such that a reaction resulting from removal is detectable, but reaction to insertion is not detectable. In other embodiments, an additional member may be wrapped around the capture mechanism 1100 as a means of detecting the spinal surgical screw 10 or other medical device has been removed.

One or more of the fingers 1102, the periphery 1101, and additional members of some embodiments are configured to at least one of rupture, non-resiliently deform, or change color when the capture mechanism 1100 is separated from a medical device that has been captured within the capture mechanism 1100. A rupture can be a full or partial rupture of all or a part of the capture mechanism 1100. Likewise, a non-resilient deformation may be a change in the shape of any part of the capture mechanism 1100 that remains thereafter in whole or in part detectable. A discoloration may occur, for example and without limitation, when a polymer material undergoes plastic material deformation. By way of example and without limitation, upon removal of a spinal surgical screw 10, one or more of the fingers 1103 may be broken off, deformed, stretched, or otherwise altered. A tracking device of any of the types previously disclosed may be associated with the capture mechanism 1100.

Figure 15:
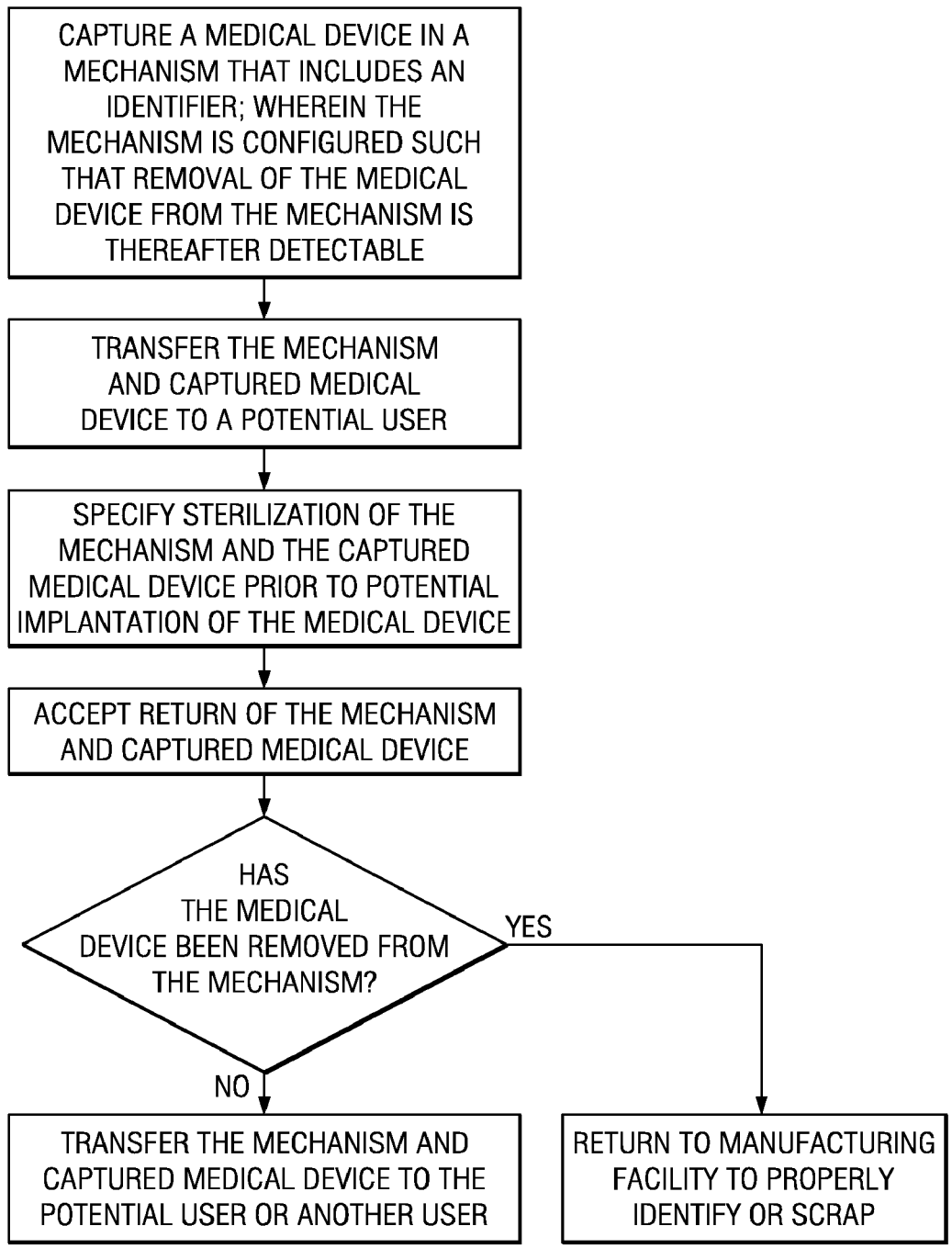
FIG. 15 is a flowchart directed to method embodiments of the invention.

FIG. 15 graphically illustrates a method of tracking a medical device. The method includes capturing the medical device in a mechanism that includes an identifier, wherein the mechanism is configured such that removal of the medical device from the mechanism is thereafter detectable. The medical device captured may be similar to any of the medical devices illustrated in FIGS. 1, 3, 5, and 7-14, any medical device otherwise described herein, or any medical device suitable to receive an identifier.

The method of some embodiments also includes transferring the mechanism and captured medical device to a potential user. A mechanism and medical device may be transferred to a user who has purchased the medical device, who has accepted the medical device on consignment, who is receiving the medical device on loan, or who is otherwise in authorized possession of the medical device. A user under various embodiments of the invention may be a specific physician, a group of physicians, a hospital, a clinic, a governmental agency, or any person or group administering receipt of medical devices. The method may further include specifying sterilization of the captured medical device prior to potential implantation of the medical device. The form of sterilization may be particularly specified, or may be left to the discretion of the user.

Method embodiments may also include accepting return of the mechanism and captured medical device. The original manufacturer or provider of the medical device would typically accept return. However, as understood herein, accepting return may also include return being accepted by an agent or otherwise authorized party acting on behalf of the original manufacturer or provider of the medical device. In some, but not all instances, return of medical devices is a result of a provider sending multiple sizes and/or configurations of a medical device to a user with an understanding that not all of the medical devices will be employed in a planned procedure.

As shown in FIG. 15, some embodiments of the invention further include checking one or both of the medical device and the mechanism to determine if the medical device has been removed from the mechanism. Such a check may include one or more of determining if the mechanism is currently present and determining if the mechanism has been previously removed from the medical device. If the medical device has been removed from the mechanism, the medical device may be returned to a manufacturing or processing facility to be identified properly, or scrapped if tracking has been lost for the device. If the medical device has not been removed from the mechanism, a method under the invention may include subsequently transferring a previously delivered and returned mechanism and captured medical device to a previous potential user or to a new user. The term new user as used herein may also refer to a new potential user. The step of checking the medical device and mechanism for removal may occur at different or additional times in some other embodiments of the invention in order to verify continued, accurate tracking of a medical device.

Some embodiments of the invention may also include maintaining a record of the identifier, and therefore, maintaining a record of the medical device that has been associated with the identifier and the mechanism in which the identifier is embodied. Consequently, by maintaining a record of the identifier, information associated with the medical device may be effectively maintained. The types of information that may be maintained in certain embodiments include the location of the identifier and medical device at a particular time, the patient or patients in or on whom a medical device has been used, and the healthcare provider or providers who have used or handled a device. A healthcare provider may include physicians, nurses, technicians, hospitals, purchasing agents, governmental agencies, administrative staff, and others. Tracked information associated with a medical device may also include a date of use, a time of use, a condition treated, a particular surgical procedure, a procedure type, a number of times sterilized, and other information that might be useful in tracking the safety, utility, and efficacy of a medical device. An identifier and medical device may also be associated in some embodiments with manufacturing information, such as but not limited to, material type, lot number, country where manufactured, manufacturing facility, time of manufacture, and manufacturing process employed.

Figure 16:
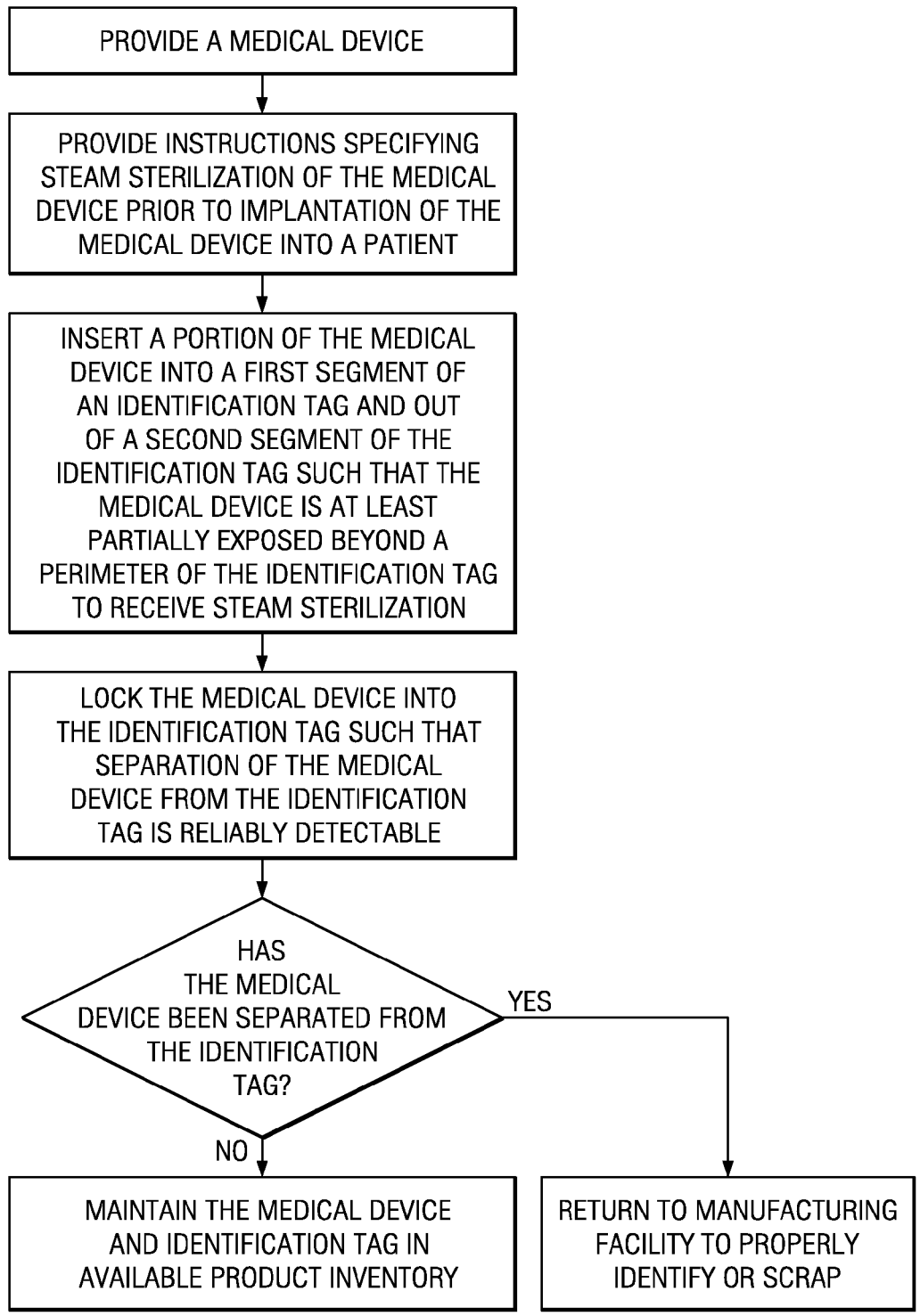
FIG. 16 is a flowchart directed to method embodiments of the invention.

A flowchart depicting another method of tracking a medical device is shown in FIG. 16. Embodiments of the method include providing a medical device and providing instructions specifying steam sterilization of the medical device prior to implantation of the medical device into a patient. Some embodiments of the method include inserting a portion of the medical device into a first segment of an identification tag and out of a second segment of the identification tag. The identification tag and medical device of such embodiments may be of any shape and size that meet the specified insertion criteria. A segment as used herein describes any portion of an identification tag, including other devices used to connect an identification tag to a medical device. Embodiments of the device are configured such that the medical device is at least partially exposed beyond a perimeter of the identification tag to receive steam sterilization. A perimeter of the identification tag may include boundaries logically drawn between irregularly shaped parts of an identification tag.

In a further step of some embodiments, the medical device is locked into the identification tag such that separation of the medical device from the identification tag is reliably detectable. Such reliably detectable structures are defined herein and include other structures performing similar functions. Method embodiments may also include detecting if the medical device has been separated from the identification tag. If the medical device has not been separated from the identification tag, a method under the invention may include maintaining the medical device in available product inventory. In some embodiments, the medical device is maintained in available product inventory with the same identification tag, and in others, it may be reassigned another identification tag. If the medical device has been separated from the identification tag, the medical device may be returned to a manufacturing or processing facility to be identified properly, or scrapped if tracking has been lost for the device. The term new user as used herein may also refer to a new potential user. The step of checking the medical device and identification tag for separation may occur at different or additional times in some other embodiments of the invention in order to verify continued, accurate tracking of a medical device.

In any of the embodiments of the present invention, the medical devices may include, be made of, treated, coated, filled, used in combination with, or have a hollow space or opening for containing artificial or naturally occurring materials and/or substances suitable for implantation in the human body. These materials, and/or substances, may include any source of osteogenesis, bone growth promoting materials, bone derived substances or products, demineralized bone matrix, mineralizing proteins, ossifying proteins, bone morphogenetic proteins, hydroxyapatite, genes coding for the production of bone, and bone including, but not limited to, cortical bone, antibiotics, cancer treating substances, infection treating substances, substances to therapeutically affect clotting or stenosis, or other disease treating substances. The medical devices can include, at least in part materials that are bioabsorbable and/or resorbable in the body.

While the invention has been described with reference to particular embodiments, it will be appreciated by those of ordinary skill in the art that various modifications can be made to the invention itself without departing from the spirit and scope thereof. All changes and modifications that are within the spirit of the invention are hereby anticipated and claimed.

What is claimed is:

1. A medical device tracking system comprising:
   a medical device; and
   a capture mechanism removably coupled to the medical device comprising:
      a body capable of multiple fluid sterilizations without degradation, and
      an identification tag associated with the body,
      wherein the capture mechanism is configured to at least in part non-resiliently deform when removed from the medical device such that removal of the medical device from the capture mechanism is thereafter detectable.

2. A medical device tracking system comprising:
   a medical device; and
   a capture mechanism removably coupled to the medical device comprising:
      a body capable of multiple fluid sterilizations without degradation, and
      an identification tag associated with the body,
      wherein the capture mechanism is configured to at least in part change color when removed from the medical device such that removal of the medical device from the capture mechanism is thereafter detectable.

3. A method of tracking a medical device comprising:
   capturing the medical device in a mechanism that includes an identifier, wherein the mechanism is configured such that removal of the medical device from the mechanism is thereafter detectable;
   transferring the mechanism and captured medical device to a potential user;
   specifying sterilization of the medical device prior to potential implantation of the medical device;
   accepting return of the mechanism and captured medical device; and transferring the mechanism and captured medical device to the potential user or another user.

4. The method of claim 3 further comprising checking one or both of the medical device and the mechanism to determine if the medical device has been removed from the mechanism.

5. The method of claim 3 further comprising maintaining a record of the identifier.

6. The method of claim 5 wherein maintaining a record includes tracking the present location of the identifier.

7. The method of claim 5 wherein maintaining a record includes associating the identifier with one or more of a patient, a healthcare provider, a date of use, a time of use, a condition treated, a surgical procedure, a procedure type, and a number of times sterilized.

8. The method of claim 3 further comprising associating the identifier and the medical device with manufacturing information.

9. A method of tracking a medical device comprising:
providing a medical device;
providing instructions specifying steam sterilization of the medical device prior to implantation of the medical device into a patient;
inserting a portion of the medical device into a first segment of an identification tag and out of a second segment of the identification tag such that the medical device is at least partially exposed beyond a perimeter of the identification tag to receive steam sterilization; and
locking the medical device into the identification tag such that separation of the medical device from the identification tag is reliably detectable.

10. The method of claim 9 further comprising detecting if the medical device has been separated from the identification tag.

* * * * *